United States Patent [19]

Gold et al.

[11] 4,215,439

[45] Aug. 5, 1980

[54] SEMI-RESTRAINING KNEE PROSTHESIS

[75] Inventors: Barry L. Gold, Warsaw; Richard C. Bolesky, Rolling Hills, both of Ind.

[73] Assignee: Zimmer, USA, Warsaw, Ind.

[21] Appl. No.: 951,860

[22] Filed: Oct. 16, 1978

[51] Int. Cl.² ............................................. A61F 1/24
[52] U.S. Cl. .................................. 3/1.911; 128/92 C
[58] Field of Search ............................... 3/1.911, 1.91; 128/92 C

[56] References Cited

U.S. PATENT DOCUMENTS

| 3,728,742 | 4/1973 | Averill et al. | 3/1.911 |
| 3,748,662 | 7/1973 | Helfet | 128/92 C X |
| 3,795,922 | 3/1974 | Herbert et al. | 3/1.911 |
| 3,816,855 | 6/1974 | Saleh | 3/1.911 |
| 4,081,866 | 4/1978 | Upshaw et al. | 3/1.911 |

FOREIGN PATENT DOCUMENTS

| 2452412 | 5/1976 | Fed. Rep. of Germany | 3/1.911 |
| 2288509 | 5/1976 | France | 3/1.911 |
| 1333412 | 10/1973 | United Kingdom | 3/1.911 |

*Primary Examiner*—Ronald L. Frinks
*Attorney, Agent, or Firm*—Trexler, Wolters, Bushnell & Fosse, Ltd.

[57] ABSTRACT

A surface replacement knee joint prosthesis is provided which restrains axial and lateral rotation of the knee joint when the leg is fully extended, and superior-inferior dislocation at all times. The prosthesis has femoral and tibial members articulated by spaced spheroidal load-sharing condylar surfaces with substantially matching radii of curvature. The femoral member defines a tapering channel positioned between the spaced condylar surfaces. A stem having a truncated head projects superiorly from the tibial member and progressively engages the tapering channel during extension, for restraining the rotation and dislocation of the knee joint when the leg is fully extended. When the leg is in flexion, the clearance between the stem and the diverging arms which define the channel allows axial and lateral rotation as in a natural knee joint.

3 Claims, 8 Drawing Figures

SEMI-RESTRAINING KNEE PROSTHESIS

BACKGROUND OF THE INVENTION

This invention relates generally to surgical joint prosthesis and especially to implant devices that are intended for substantially total replacement of the surfaces of a diseased or traumatized human knee.

Much medical interest in total joint replacement has been generated in the course of the past decade, originally stimulated to a large degree by the successes of John Charnley with total hip joint replacement. The concept of total joint replacement has been extended from hips to encompass knees, shoulders, ankles and elbows. Moreover, total joint repair has been increasingly applied to younger patients. Not unexpectedly, the number of prosthesis arrangements has proliferated apace with these conceptual advances and the United States patent literature is replete with examples of knee replacement prosthesis, including the following: Moritz U.S. Pat. No. 3,694,821; Herbert et al U.S. Pat. No. 3,795,922; and Kaufer et al U.S. Pat. No. 3,868,720.

The human knee is generally recognized as being an inherently unstable joint which is normally capable, nevertheless, of accommodating complex motions and successfully accepting substantial physical stress loads. Despite the rather appreciable efforts made in the past to develop an artificial total knee replacement prosthesis and despite the variety of approaches that have been pursued, results have not heretofore been entirely satisfactory. Prior efforts have left unsolved the problem of preserving the strength and stability required when the joint is extended without sacrificing the complex motions found when the natural knee joint is in flexion. This is particularly true when the cruciate ligaments have been destroyed due to disease or trauma.

Knee prosthesis are divided generally into two types or groups, the first of which is the non-constrained or unlinked device. Here, the damaged load bearing surfaces of the knee are replaced with plastic or metal caps or molds and the stability of the joint is provided by the surrounding, intact ligaments and muscles. The non-constrained devices are often effective because of their wide load bearing surfaces and approximation of natural joint movement. In addition, as only the articulating surfaces of the knee joint are replaced, the bone removal upon installation is minimal. Thus, the inherent strength of the surrounding bone supports the prosthesis and the availability of future surgical alternatives is retained. However, if the remaining ligaments are insufficient to insure joint stability or if the articular surfaces are severly impaired, a prosthesis with a mechanical linkage between the femoral and tibial components has heretofore been required. These latter devices, termed "constrained", necessitate substantial bone removal with attendant difficulties upon any subsequent surgical revision.

Examples of the constrained or linked design include the Walldius prosthesis which employs a simple fixed horizontal hinge to afford joint stability in the absence of supporting ligaments. However, since, during flexion of the natural knee joint, the center of rotation moves in a posterior spiral curve, the single axis hinge in the Walldius-type knee cannot approximate the complex polycentric rotation of a normal knee. In addition, as a fixed hinge is rigid in all positions, The Walldius design cannot allow the axial and lateral freedom of movement found in the natural knee.

The patent to Moritz U.S. Pat. No. 3,694,821 discloses a multi-chambered ball-and-socket joint for more closely approximating these polycentric tri-axial movements. However, ball-and-socket joints designed small enough to be placed within the human knee have proved oftentimes to be structurally insufficient to sustain the dynamic loads imposed upon the knee joint during normal activities. Also, due to the spherical shape of the articulating portion, when such a joint is implanted, considerable bone must be removed, especially from the distal femur; and this results in a loss of structural support for the prosthesis and substantially limits future surgical alternatives. In addition, while the Moritz ball-and-socket device permits triaxial movement when the joint is in flexion, it fails to limit such movements upon extension to provide the rigid lateral stability of the extended natural knee.

The device of the patent to Herbert et al U.S. Pat. No. 3,795,922 attempts to provide extensile stability in a ball-and-socket prosthesis by the use of engaging locking members disposed between the femoral and tibial components. However, in addition to suffering from the above-mentioned structural deficiencies inherent in all ball-and-socket prostheses, the Herbert device requires substantially more bone removal to accommodate the additional locking members.

The patent to Kaufer et al U.S. Pat. No. 3,868,730 teaches the use of primary load bearing surfaces arranged on either side of the ball-and-socket linkage which are similar in shape to those in the natural knee joint. However, the Kaufer prosthesis posesses the disadvantage inherent in all of the linked or constrained knee prostheses heretofore employed, i.e. the centers of rotation of the prosthesis are substantially above the tibial plateau and the ball and the socket must be implanted well into the femur to approximate natural movement. Also, as the Kaufer knee provides a plastic lining or insert between the ball and the socket, the overall size of the femoral member is accordingly increased and greater amounts of supporting bone must be removed when the knee is implanted. In addition, the femoral socket member is generally supported by an elongate fixation stem which is driven superiorly into the cortical bone of the femur.

Thus, the linked prosthetic knee requires a substantial sacrifice of supporting bone structure. After such a device is installed, future surgical alternatives become limited and fusion of the knee or arthrodesis becomes virtually impossible.

It is therefore a general object of the present invention to provide a new and improved knee prosthesis.

Another object of the present invention is to provide a surface replacement knee prosthesis which mechanically limits dislocation of the load bearing surfaces.

Another object of the present invention is to provide a total knee prosthesis which affords axial and lateral rotation in flexion while substantially limiting such rotations upon extension.

Still another object of the present invention is to provide a semi-restraining knee prosthesis which requires minimal bone removal and resectioning upon installation.

BRIEF DESCRIPTION OF THE DRAWINGS

In order that the principles of the present invention may be readily understood, a single embodiment thereof, applied to a knee prothesis, but to which the application is not to be restricted, is shown in the accompanying drawings wherein.

DETAILED DESCRIPTION OF THE ILLUSTRATED EMBODIMENT

Figure 1:
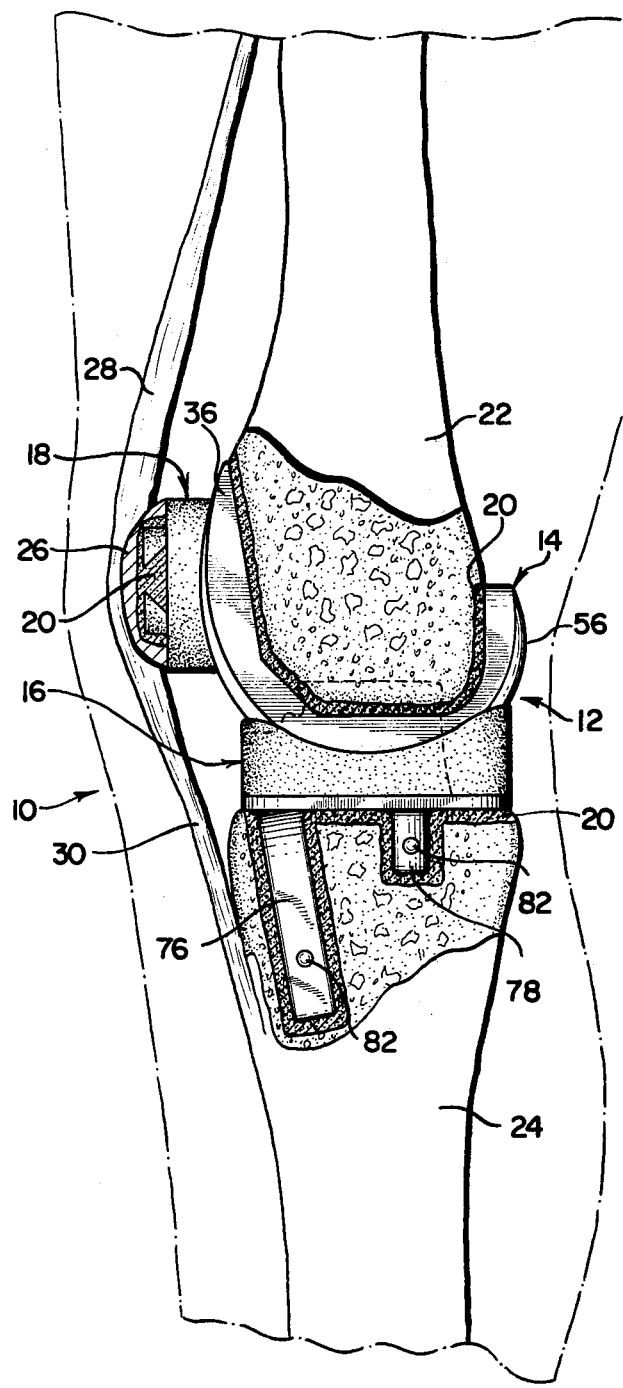
FIG. 1 is a sagittal, partial sectional view representing a human knee implanted with a semi-restraining total knee prosthesis constructed in compliance with the present invention.

Referring now in detail to the drawings, specifically to FIG. 1, the knee joint of a human right leg is illustrated and there indicated generally by the reference numeral 10. The knee joint 10 is shown to have been repaired by a semi-restraining total joint prosthesis 12 that is constructed in compliance with the present invention. Total knee prosthesis 12 comprises a femoral component 14 which is advantageously fabricated from a medically suitable metal alloy, such as a chromium-cobalt alloy; a tibial plateau component 16 which is cooperatively fashioned from a suitable polymeric resinous plastics material, such as, for example, high density or ultra-high molecular weight polyethylene; and a patellar piece component 18 which is also made from such a resinous plastics material. When fabricated as described, the components of the prosthesis 12 avoid metal-to-metal contact and thus promote smooth interaction of the respective articular surfaces.

Repair of the knee 10 will have been medically indicated previously, as by some substantial degree of disfunction resulting from a traumatic injury or from a progressive disease; and in the initial stages of surgery, certain structures in the knee joint will be removed selectively preparatory to installing the prosthesis 12, advantageously utilizing fixation by means of suitable quantities of bone cement 20. Various cooperating fixation structures are incorporated in the components of the prosthesis 12, as will be described more fully hereinafter, in order to promote secure installation. It is, however, important at this juncture to appreciate that the femoral component 14 is affixed to the distal end of femur 22 to replace the condylar surfaces thereof, that the plateau component 16 is affixed to the head of tibia 24 in substitute for the cartilaginous articular surfaces thereof, and that the patellar piece component 18 is secured to the posterior side of the natural patella 26 so as to assure desirable continuity of the quadriceps tendon 28 and the patellar ligament 30.

Figure 2:
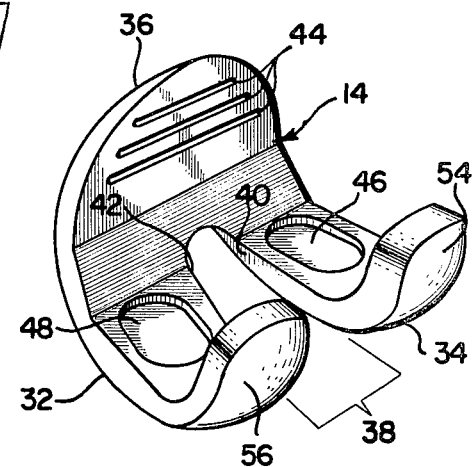
FIG. 2 is a perspective view of the femoral component of the knee prosthesis of FIG. 1, illustrating the fixation structures used in mounting the component in place at the distal end of the femur and showing the posterior taper of the two claw arms.
Figure 3:
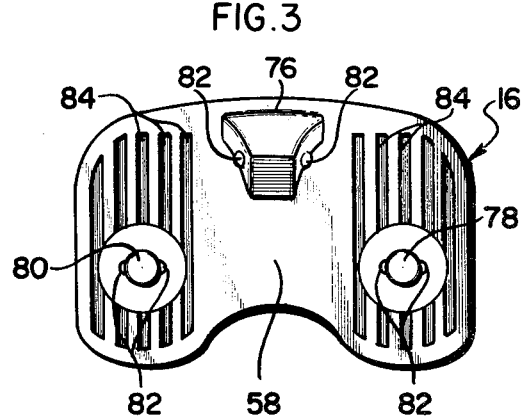
FIG. 3 is a bottom plan view of the tibial plateau component of the knee prosthesis of FIG. 1, illustrating the fixation structures used in mounting the component in place at the proximal end of the tibia.
Figure 4:
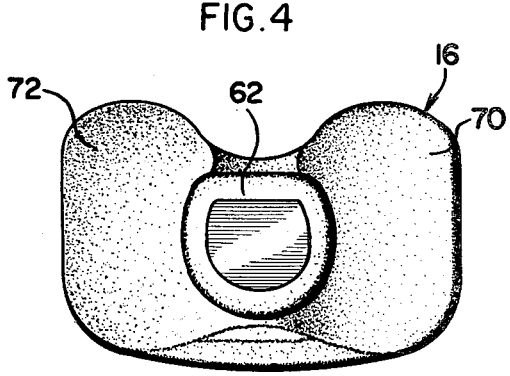
FIG. 4 is a top plan view of the tibial plateau component.

Turning to FIG. 2 for a more detailed description of the femoral component 14, that member is seen to comprise a pair of convex articular surface defining elements 32 and 34, which are connected by an anteriorly situated patellar plate portion 36 comprising a bridge. In compliance with the principles of the present invention, the convex articular surface elements 32 and 34 are separated posteriorly by a tapered slot 38 defined by laterally opposed claw arms 40 and 42. As a consequence, the articular surface elements 32 and 34 are exclusively connected by the patellar plate portion 36.

Figure 6:
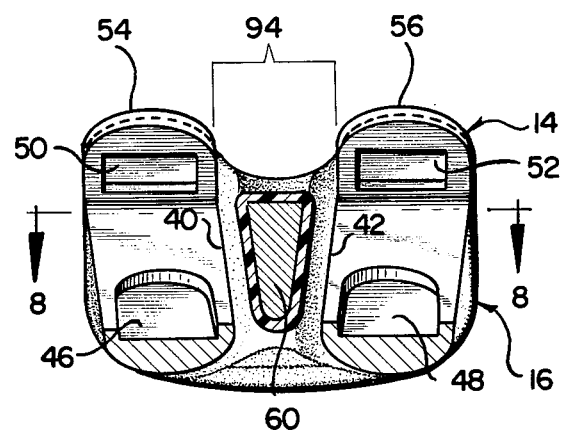
FIG. 6 is a top view of the assembled femoral and tibial components of the knee prosthesis of FIG. 1 with the stem portion of the tibial component and the femoral component partially in section as would appear with knee joint in partial flexion.

As an aid in fixation of the component 14, cement receiving grooves 44 are relieved into the posteriorly facing surface of patellar plate portion 36 and cement-receiving niches 46 and 48 are relieved into the proximally facing surfaces of elements 32 and 34. Similar niches 50 and 52 are formed in the anteriorly facing surfaces of the upturned ends 54 and 56 of the convex articular surface elements 32 and 34 respectively, as is best seen in FIG. 6.

Returning to FIG. 1, patellar plate portion 36 is provided with a smoothly curved anterior surface which is adapted to coact with an appropriately configurated groove in the patellar piece component 18 in fittably gliding relationship. Patellar piece component 18 is suitably installed posteriorly of the natural patella 26 by means of bone cement 20.

The construction of the tibial plateau component 16 will now be described with reference to FIGS. 3 thru 8 inclusive. The tibial plateau component 16 specifically comprises a rigid support base 58, preferably fabricated from tissue-compatible metal and advantageously having a central stem portion 60 fashioned with a truncated head 62, a shank of triangular cross-section beneath the head 62, and spaced plateau support portions 64 and 66. In the preferred construction, base 58 achieves bearing support for articulating polymeric surface means suitably attached to base 58 and comprising plateau portions 70 and 72 and an anti-friction stem covering 74.

In order to promote secure fixation of the component 16 in the bony head of the tibia, support base 58 is fabricated with an anterior stem 76 and medial and lateral fixation posts 78 and 80, each of which includes abbreviated hemispheric fixation protrusions or buttons 82. Base 58 also includes cement receiving grooves 84, stem 76 and posts 78 and 80 being provided for situation in apertures surgically excavated in the bony head of the tibia by means of bone cement 20, as is shown in FIG. 1.

In compliance with the present invention, the femoral and tibial components of the prosthesis 12 are fashioned with congruent articular surfaces; and therefore, the plateau portions 70 and 72 of tibial component 16 define respective concave articular surfaces 86 and 88 having curvatures substantially matching the convex articular surface of elements 32 and 34 of femoral component 14.

Figure 5:
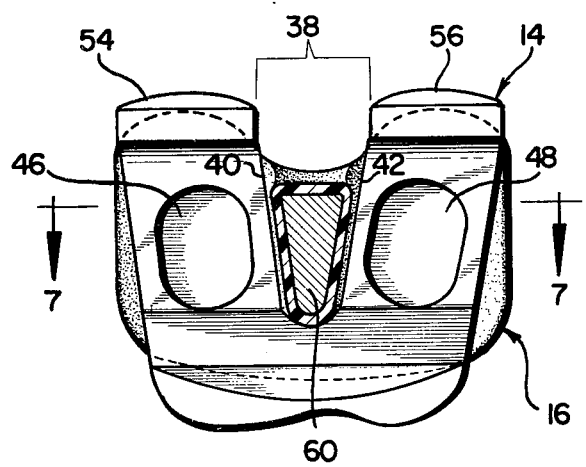
FIG. 5 is a top view of the assembled femoral and tibial components of the knee prosthesis of FIG. 1 with the stem portion of the tibial component illustrated in section to show the nearly fully extended position of knee joint articulation.
Figure 7:
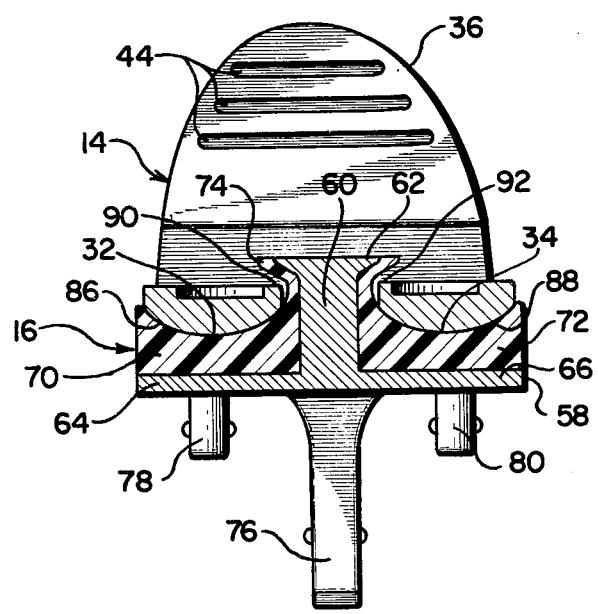
FIG. 7 is a sectional view taken along the line 7—7 of FIG. 5 to show the intimate mating engagement of the femoral and tibial components.

As will be seen in FIGS. 5 and 7, detailing the prosthesis with the knee extended, the opposed claw arms 40 and 42 of the femoral component 14 form the walls of tapered slot 38 which walls matably impinge against the wedged shape of stem 60 of tibial component 16 to limit the axial rotation of the knee joint. In addition, as shown in FIG. 7, the truncated head 62, through polymeric stem covering 74, applies an even downward force to wedge-shaped condylar portions 90 and 92 of femoral component 14. This causes the convex articular surface of elements 32 and 34 to be held tightly against concave articular surfaces 86 and 88 whereby to eliminate medial-lateral rotation of the knee upon extension.

Figure 8:
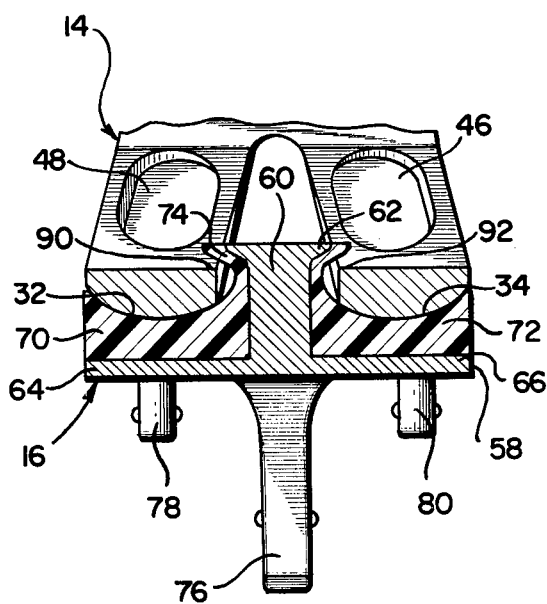
FIG. 8 is a sectional view taken along the line 8—8 of FIG. 6 to show the limited motile freedom of the femoral and tibial components.

As is detailed in FIGS. 6 and 8, when flexion of the knee is initiated, the femoral component 14 moves relative to tibial component 16 so that upturned ends 54 and 56 begin to bear on concave articular surfaces 86 and 88. Thus, the opposed claw arms 40 and 42 begin to move away from stem 60 to form a progressively laterally and medially enlarging free space 94 which allows limited axial rotation of the knee joint. As is shown in FIG. 8, truncated head 62 also moves away from wedged engagement with the condylar portions 90 and 92 reducing the "claw hammer" effect and allowing a natural medial-lateral rotation of components 14 and 16.

The articular surfaces of elements 32 and 34 of femoral component 14 and surfaces 86 and 88 of tibial component 16 are deeply mating throughout the transit of the knee joint prosthesis from full extension through flexion. The repaired knee thus distributes the massive forces of articulation over a comparatively large area. The resultant attenuation of friction minimizes the possible wear of engaging parts and prolongs their useful life.

As the knee prosthesis 12 approaches full extension, claw arms 40 and 42 and condylar portions 90 and 92 of femoral component 14 progressively engage the stem 60 beneath and in progressive contact with the undersurface of the truncated head 62 of tibial component 16 whereby to limit the motile freedom of the flexed knee and provide a natural locking engagement upon full extension.

The drawings and the foregoing descriptions are not intended to represent the only form of the invention in regard to the details of its construction and manner of use. Changes in form and in the proportion of parts, as well as the substitution of equivalents, are contemplated as circumstances may suggest or render expedient; and although specific terms have been employed, they are intended in a generic and descriptive sense only and not for purposes of limitation, the scope of the invention being delineated in the following claims.

The invention is claimed as follows:

1. A surface-replacement knee joint prosthesis comprising: a tibial component including medial and lateral articulate surface means of concave configuration, and bridge means rigidly mechanically interconnecting said surface means; a surface-replacement femoral component including medial and lateral articular surface means of convex configuration congruent with said concave tibial surface means for matably bearing engagement respectively with said medial and lateral tibial surface means, and bridge means rigidly mechanically interconnecting said femoral articular surface means; and restraining means acting between said femoral and tibial components for preventing superior-inferior and lateral-medial dislocation of said components and for defining limited superior-inferior motile freedom during flexion of the knee joint and for incurring progressively more intimate mating engagement of said femoral and tibial articular surfaces as said knee joint rotates from flexion into extension, including a stem portion having a shank of triangular cross-section and a truncated head and including a cooperating pair of opposed claw arms defining a posteriorly divergent, tapered slot therebetween for progressively receiving said shank in the lateral-medial plane as full extension is approached, said claw arms defining wedge-shaped formations for use in incurring said progressive engagement and said motile freedom.

2. A surface-replacement knee joint prosthesis according to claim 1 wherein said stem portion is mounted on said tibial component and wherein said claw arms are joined to said femoral surface means.

3. A surface-replacement knee joint prosthesis according to claim 1 wherein said femoral bridge means is a patellar plate member.

* * * * *